US00PP16092P2

(12) United States Plant Patent
Olesen et al.

(10) Patent No.: US PP16,092 P2
(45) Date of Patent: Nov. 1, 2005

(54) ***CLEMATIS* PLANT NAMED 'EVIPO003'**

(50) Latin Name: ***Clematis* hybrid**
Varietal Denomination: Evipo003

(75) Inventors: Mogens N. Olesen, Fredensborg (DK); Raymond J. Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 85 days.

(21) Appl. No.: 10/884,346

(22) Filed: Jul. 1, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar with compact growth habit, profuse, white and violet blue flowers which is well suited to propagation in glasshouses. The variety successfully propagates from softwood cuttings and is suitable for cultivation in commercial glasshouses. This new and distinct variety has shown to be uniform and stable in the resulting generations from asexual propagation.

3 Drawing Sheets

Botanical classification: *Clematis l.* Genus—*Clematis.* Species—hybrid.
Variety denomination: 'Evipo003'.
Commercial classification: Early flowering cultivar.

SUMMARY OF THE INVENTION

The present invention constitutes a new and distinct variety of *Clematis* which originated from a controlled crossing between the female parent 'Evitwo' described and illustrated in U.S. Plant Pat. No. 10,167 dated Dec. 30, 1997, and the male parent, an unnamed, unpatented plant of *Clematis chrysocoma* a non-patented *clematis.*

The new *clematis* may be distinguished from its female seed parent, 'Evitwo', by the following combination of characteristics:

1. 'Evipo003' is a single flowered variety, whereas 'Evitwo' is a double flowered variety.
2. While flowers of 'Evitwo' are pure white, 'Evipo003' has violet intonations in the tepals.

The new *clematis* may be distinguished from its male pollen parent, *Clematis chrysocoma*, by the following combination of characteristics:

1. *Clematis chrysocoma* has pink flowers, while 'Evipo003' has white and violet blue flowers.
2. 'Evipo003' has a greater flower size than *Clematis chrysocoma.*

The two parents were crossed and the resulting seed was planted in a controlled environment. The new variety is named 'Evipo003'.

The objective of the hybridization of this *Clematis* variety for commercial glasshouse and nursery culture was to create a new and distinct variety with unique qualities that this variety has:

1. Profuse flowering habit.
2. White flowers with slight violet blue tones and a yellow center.

These qualities required improvement in *Clematis* varieties that were in commercial cultivation and the objectives have been substantially achieved in the new variety, as evidenced by the unique combination of characteristics that are present in 'Evipo003' which distinguish it from all other varieties of which we are aware.

The seeds from the aforementioned hybridization were germinated and evaluations of the resulting seedling plants were conducted in a controlled environment. As a result, 'Evipo003' was selected by Raymond J. Evison and Mogens N. Olesen in their *Clematis* development program in Domarie Vineries Les Sauvagees, St. Sampsons, Guernsey, Channel Islands, United Kingdom in April 1998.

Asexual reproduction of 'Evipo003' by cuttings was first done by Raymond J. Evison and Mogens N. Olesen in Domarie Vineries Les Sauvagees, St. Sampsons, Guernsey, Channel Islands, United Kingdom in May 1998. This initial and subsequent asexual propagations have demonstrated that the characteristics of 'Evipo003' are true to type and are transmitted from one generation to the next.

BRIEF DESCRIPTION OF THE DRAWING

The accompanying color illustrations show as true as is reasonably possible to obtain in color photographs of this type:

FIG. 3.1 Stem, leaves, bud at ¼ opening, bud closed;
FIG. 3.2 Mature stem and leaves;
FIG. 3.3 Juvenile stem and leaves.

DETAILED DESCRIPTION OF THE VARIETY

Figure 1:
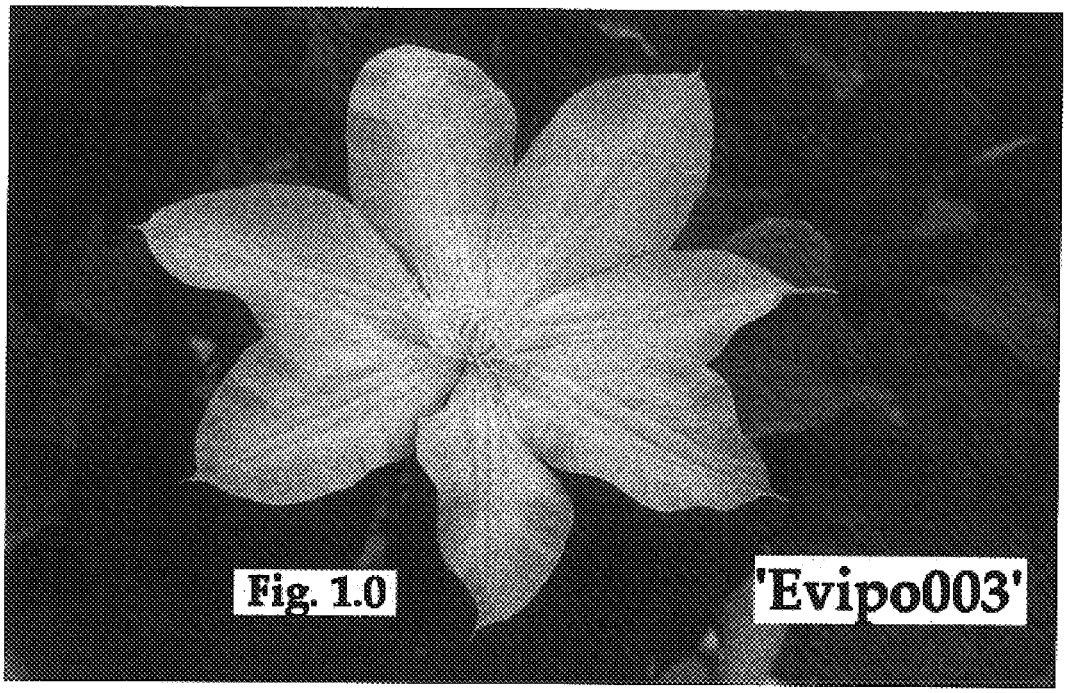
FIG. 1 Open flower upper side.
Figure 2:
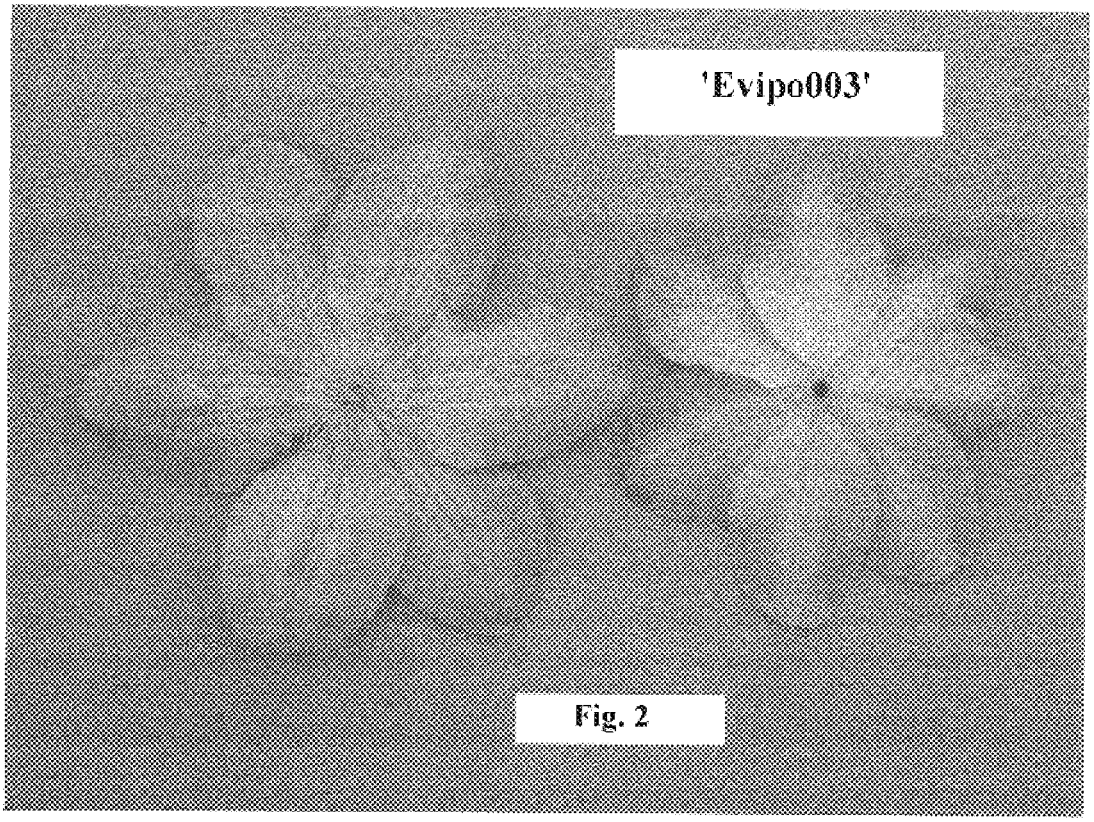
FIG. 2 Open flower, upper and lower surface.

The following is a detailed description of 'Evipo003', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Evirin', a patented variety described and illustrated in U.S. Plant Pat. No. 12,838 issued on Aug. 13, 2002. Chart 1 details several physical characteristics of 'Evipo003' and the comparison variety.

CHART 1

| | 'Evipo003' | 'Evirin' |
|---|---|---|
| Anther color | Yellow | Dark Red |
| Season's growth | 1.5 to 2 M | 2.5 M |

FLOWER AND FLOWER BUD

Blooming habit: Recurrent. Normally flowers April through June and September through October.

Flower bud:
- *Size.*—50 to 60 mm in length. Bud diameter is 15–20 mm.
- *Bud form.*—Long Elliptic.
- *Bud color.*—Yellow-Green Group 144C with Violet-Blue Group 97C tepal margins at ¼ opening.

Peduncle:
- *Surface.*—Smooth and pubescent.
- *Length.*—50 to 70 mm average length.
- *Color.*—Yellow-Green Group 144B.
- *Strength.*—Strong.

Receptacle: Absent.

Flower arrangement:
- *Location.*—On the vine flowering occurs on new and old growth.
- *Borne.*—Flowers normally occur singly in the spring. In the autumn, flowers occur on compound cymes in clusters of 3 to 7 flowers.

Flower bloom:
- *Size.*—120–160 mm in diameter. 15 mm in depth.
- *Profile.*—Upon opening, flowers are flat. After opening flowers are flat, with tepals somewhat reflexing.
- *Tepal color.*—Upon opening: Upper and lower surface is White Group N155A in color. Other intonations of Violet-Blue Group 92C observed at margins and tepal apex. After opening: Upper and lower surface is White Group N155A in color. Other intonations of Violet-Blue Group 92C observed at margins and tepal apex.
- *Variations.*—Uniform.
- *Fragrance.*—None.
- *Lasting quality.*—On the plant: 10 to 15 days. Cut flower: 3 to 7 days.

Tepals:
- *Quantity.*—Single. 6 to 8 tepals normally.
- *Size.*—65 to 80 mm in length by 40 to 50 mm wide on average.
- *Shape.*—Individual tepal shape is ovate.
- *Reflexing.*—Slight.
- *Cross section.*—Flat.
- *Margins.*—Entire.
- *Undulations.*—Margins undulate somewhat, 3–5 times along tepal length.
- *Tepal apex.*—Obtuse and mucronate.
- *Tepal base.*—Acute.
- *Persistence.*—Tepals drop off cleanly.
- *Arrangement.*—Tepals are arranged regularly.

Reproductive organs:
- *Arrangement.*—Open.
- *Pollen.*—Quantity: Average. Color: White Group 155A.
- *Anthers.*—Size: 5–7 mm in length. Color: Yellow Group 8C. Quantity: On average 160 to 190.
- *Filaments.*—Color: White Group N155A. Length: 15 to 18 mm.
- *Pistils.*—Quantity: 60 to 70.
- *Stigmas.*—Inferior becoming superior as flower opens.
- *Styles.*—Color: Green-White N157 A. Length: 15 to 18 mm.

Seed head characteristics:
- *Shape.*—Seed clusters are globular.
- *Individual seed size.*—7 to 9 mm in length. 5 to 7 mm in diameter at the base with a long 30 to 45 mm plumule.
- *Shape.*—Circular to tear shape.
- *Style.*—Feathery, 50–80 mm in length.

PLANT

Plant form: Climbing.

Plant growth: Moderately vigorous.

Size: Seasons growth attains 1.5 to 2.0 meters in height. Average spread is 1 meter.

Hardiness: Trials to date show the variety hardy in USDA Zones 4–9.

Stems:
- *Color.*—Juvenile: Yellow-Green Group 145B. Mature: Greyed-Orange Group 165C.
- *Internodes.*—Shape: Cylindrical. Length: 145 to 170 mm.
- *Surface texture.*—Young wood: Smooth. Older wood: Smooth.

Plant foliage:
- *Leaf characteristics.*—Deciduous. Mature leaves are normally Trifoliate. Occasionally, plants produce single leaves.
- *Compound leaf size.*—200 to 250 mm (l)×190 to 230 mm (w).
- *Abundance.*—Generally, there are 6 leaves per 250 to 300 mm of stem.
- *Color.*—Upper surfaces of mature leaves are Green Group 137A. Lower surfaces are Green Group 137C. Upper surfaces of juvenile foliage are Green Group 143A. Lower surfaces are Green Group 145A.

Plant leaves and leaflets:
- *Stipules.*—Absent.
- *Petioles.*—Average length: 90–120 mm. Color: Yellow-Green Group 144C and Red-Purple Group 71A. Clasping: By leaf petiole.
- *Petioloule.*—Length: 20 to 55 mm. Color: Yellow-Green Group 144C and Red-Purple Group 71A.
- *Leaflet shape.*—General shape: Ovate, Elliptic. Base: Rounded. Apex: Acute and acuminate.
- *Margin.*—Entire.
- *Leaflet size.*—70 to 90 mm in length by 25 to 40 mm wide.
- *Surface texture.*—Upper and lower surfaces are smooth.
- *Thickness.*—Moderate.
- *Surface appearance.*—Glossy.

Disease resistance: Subject to any disease that normally attacks the species.

We claim:

1. A new and distinct variety of *Clematis* plant, substantially as herein shown and detailed, as a distinct and novel *Clematis* variety due to its abundant white and violet blue flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

Fig. 1.0
'Evipo003'

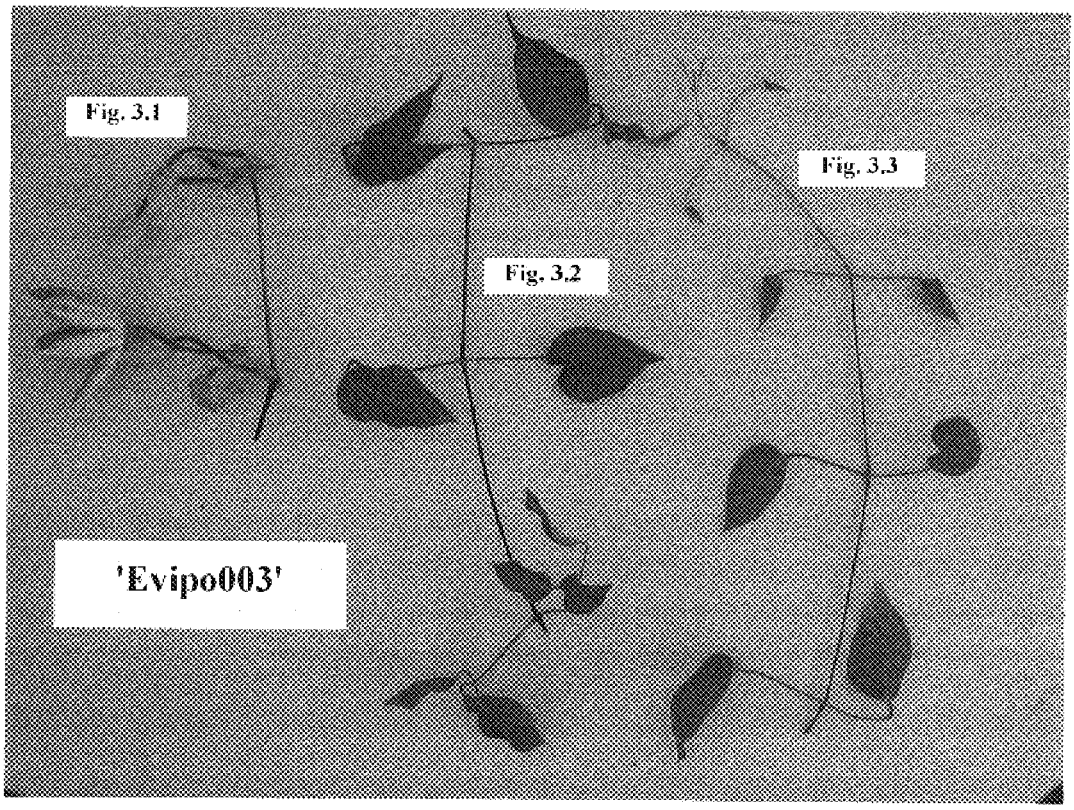
Fig. 3.1
Fig. 3.2
Fig. 3.3
'Evipo003'